US00PP25449P3

(12) United States Plant Patent
Lommerse

(10) Patent No.: US PP25,449 P3
(45) Date of Patent: Apr. 14, 2015

(54) ***GAZANIA* PLANT NAMED 'LOMGAZYLRS'**

(50) Latin Name: *Gazania splendens*
Varietal Denomination: LOMGAZYLRS

(71) Applicant: Henry Lommerse, Mariahout (NL)

(72) Inventor: Henry Lommerse, Mariahout (NL)

(73) Assignee: Lommerse Holdings B.V. (NL)

( * ) Notice: Subject to any disclaimer, the term of this patent is extended or adjusted under 35 U.S.C. 154(b) by 108 days.

(21) Appl. No.: 13/815,084

(22) Filed: Jan. 30, 2013

(65) Prior Publication Data

US 2014/0215660 P1 Jul. 31, 2014

(51) Int. Cl.
*A01H 5/00* (2006.01)

(52) U.S. Cl.
USPC ..... Plt./334

(58) Field of Classification Search
CPC ..... A01H 5/00
USPC ..... Plt./334
See application file for complete search history.

*Primary Examiner* — Anne Grunberg

(57) ABSTRACT

A new and distinct *Gazania* cultivar named 'LOMGAZYLRS' is disclosed, characterized by vigorous and strong plant habit, large flower diameter, yellow with red striped flowers and dark green fern shaped foliage. The new variety is a *Gazania*, normally produced as an outdoor garden or container plant.

2 Drawing Sheets

Figure 1:
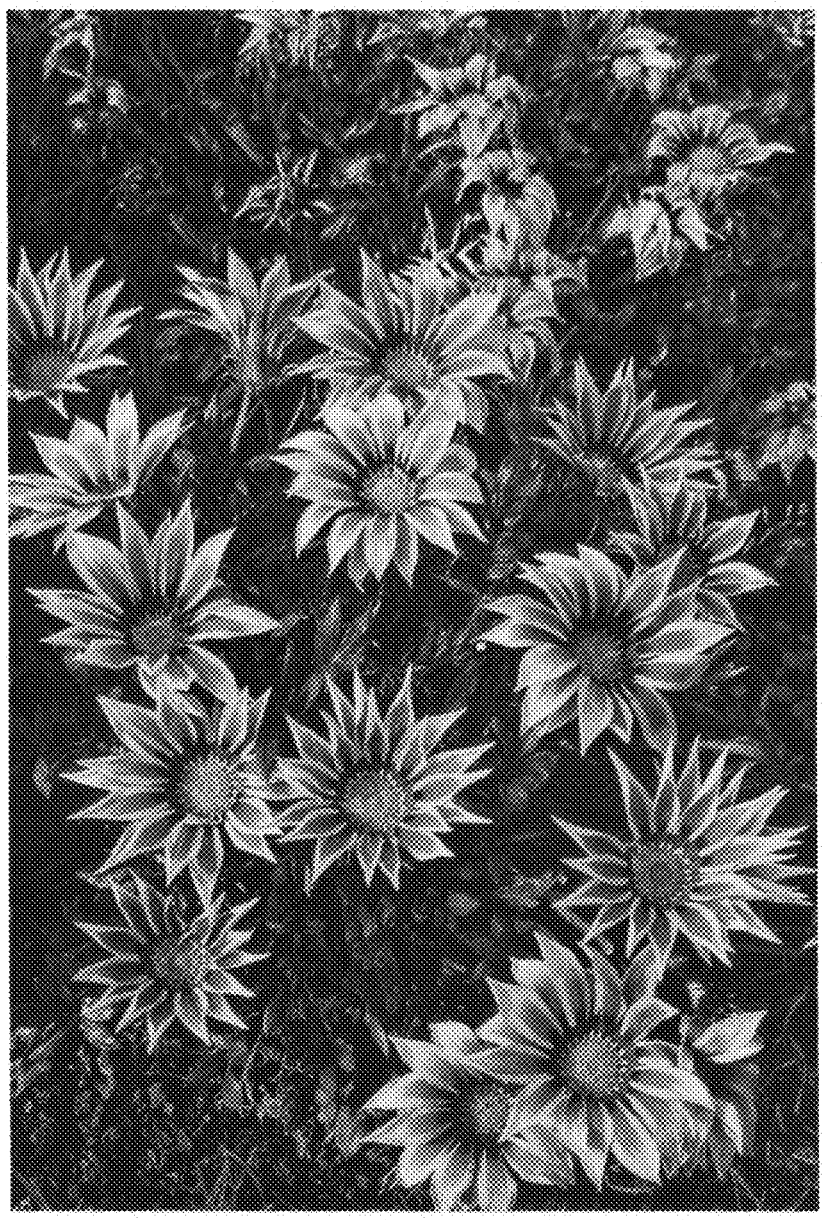

Latin name of the genus and species: *Gazania splendens.*
Variety denomination: 'LOMGAZYLRS'.

BACKGROUND OF THE INVENTION

The new *Gazania* cultivar is a product of a planned breeding program conducted by the inventor, Henry Lommerse, in a research greenhouse in Mariahout, the Netherlands. The objective of the breeding program was to produce new *Gazania* varieties. The cross resulting in this new variety was made during July of 2007.

The seed parent is the unpatented, proprietary variety *Gazania* '8152/07'. The pollen parent is the unpatented, proprietary variety *Gazania* '5706/07'. The new variety was identified as a potentially interesting selection in Jul. 15, 2008, at a research greenhouse in Mariahout, the Netherlands.

Asexual reproduction of the new cultivar 'LOMGAZYLRS' by vegetative cuttings was first performed during May of 2009, at a research greenhouse in Mariahout, the Netherlands. Subsequent propagation has shown that the unique features of this cultivar are stable and reproduced true to type on successive generations.

SUMMARY OF THE INVENTION

The cultivar 'LOMGAZYLRS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LOMGAZYLRS' These characteristics in combination distinguish 'LOMGAZYLRS' as a new and distinct *Gazania* cultivar:

1. Vigorous and strong plant habit.
2. Large flower size.
3. Yellow with red striped flower coloration.
4. Dark green fern shaped foliage.

5. Flowers stay open during a long part of the day, including dark evening hours.
6. Commercially useful as garden plant.
7. Uniquely suited for container plant use.

PARENT COMPARISON

Plants of the new cultivar 'LOMGAZYLRS' are similar to plants of the seed parent, *Gazania* '8152/07' in most horticultural characteristics, however, plants of the new cultivar 'LOMGAZYLRS' produce larger flowers with yellow with red striped coloration compared to the seed parent's yellow/bronze bicolor flowers. Additionally plants of the new variety are larger than plants of the seed parent.

Plants of the new cultivar 'LOMGAZYLRS' are similar to plants of the pollen parent, *Gazania* '5706/07' in most horticultural characteristics, however, plants of the new cultivar 'LOMGAZYLRS' produces flowers with yellow with red striped coloration compared to the pollen parent's golden yellow flower coloration. Additionally the new variety is weaker in growth compared to the pollen parent.

COMMERCIAL COMPARISON

Plants of the new cultivar are best compared to the unpatented commercial variety *Gazania* 'Gazoo Yellow'. Plants of the new variety produce larger, bicolored flowers compared to the yellow flower color of 'Gazoo Yellow'. Additionally, the new variety has more vigor, a better plant habit and better foliage durability than 'Gazoo Yellow'.

BRIEF DESCRIPTION OF THE PHOTOGRAPHS

The accompanying photograph in FIG. 1 illustrates in full color a typical plant of 'LOMGAZYLRS' grown outdoors in Mariahout, the Netherlands, in in the ground in a trial field. Age of the plant photographed is approximately 6 months from a rooted cutting.

Figure 2:
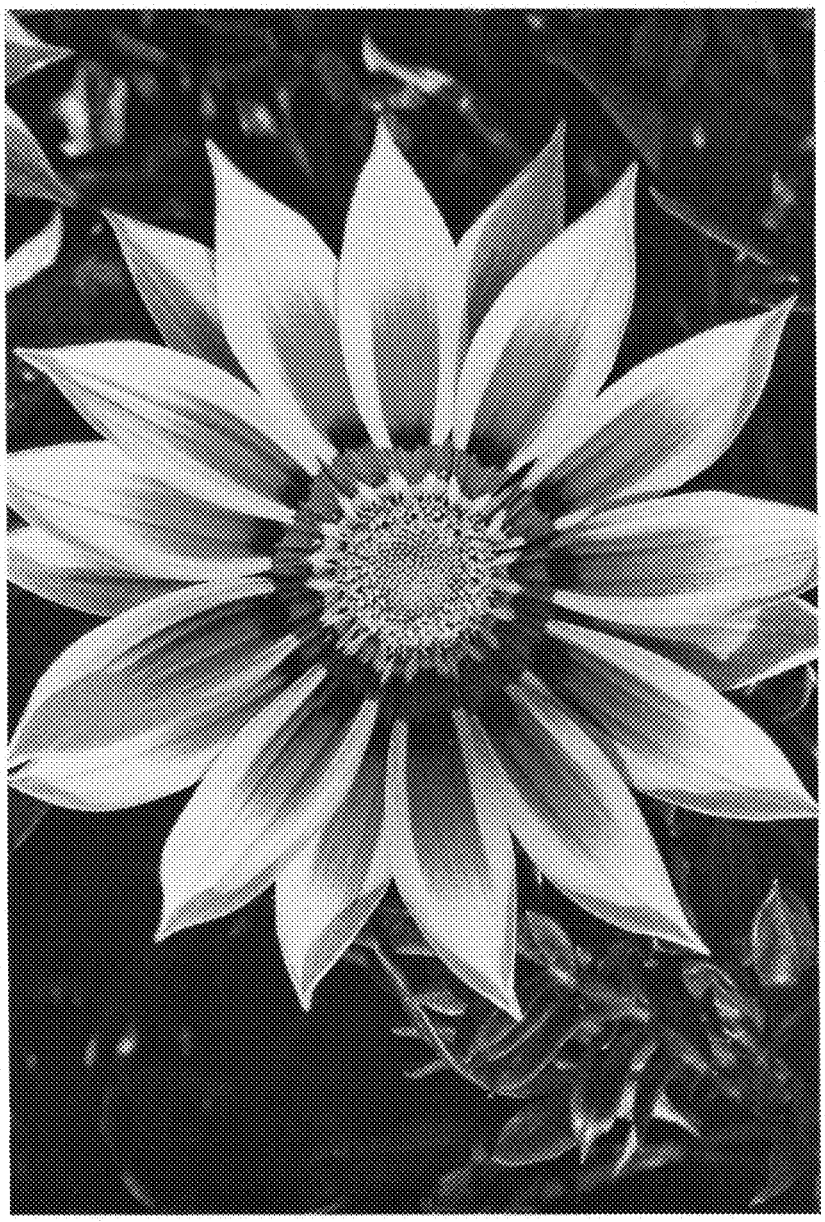

FIG. 2 illustrates in full color a typical inflorescence of 'LOMGAZYLRS'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'LOMGAZYLRS' plants grown in a commercial greenhouse in Mariahout, the Netherlands. The growing temperature ranged from 17° C. during the day to 15° C. during the night. The greenhouse is un-shaded, giving bright, normal sunlight conditions. Measurements and numerical values represent averages of typical plant types.

Botanical classification: *Gazania splendens* 'LOMGAZYLRS'.

PROPAGATION

Time to initiate roots: About 21 days at approximately 17° C.

Root description: Fine, freely branching.

PLANT

Age of plant described: 12 weeks days from a rooted cutting.

Growth habit: Upright.

Height: Approximately 21 cm.

Plant spread: Approximately 38 cm.

Growth rate: On average 3 cm per week, depends on time of year.

Branching characteristics: No branching.

FOLIAGE

Leaf:

- *Arrangement*.—Irregularly whorled, basally emerging, single.
- *Average length*.—Approximately 16 cm.
- *Average width*.—Approximately 4 cm.
- *Shape of blade*.—Oblanceolate.
- *Apex*.—Acute.
- *Base*.—Attenuate.
- *Attachment*.—Stalked.
- *Margin*.—Entire.
- *Texture of top surface*.—Glabrous.
- *Texture of bottom surface*.—Glabrous.
- *Appearance top surface*.—Glossy.
- *Appearance bottom surface*.—Shiny.
- *Leaf internode length*.—Approximately 0.3 to 1 cm.
- *Color*.—Young foliage upper side: Near RHS Green 137 A. Young foliage under side: Near RHS Green 138 C. Mature foliage upper side: Near RHS Yellow-Green 147 A. Mature foliage under side: Near RHS Yellow-Green 147 D.
- *Venation*.—Type: Pinnate. Venation color upper side: Indistinguishable from leaf blade.
- *Venation color under side*.—Indistinguishable from leaf blade.

Petiole:

- *Length*.—2.5 cm.
- *Diameter*.—0.3 cm.
- *Pubescence*.—No.
- *Color*.—Near RHS Yellow-Green 144 A.

FLOWER

Natural blooming season: Spring and Summer.

Flower form: Daisy-type composite inflorescence form. Inflorescences solitary. Ray and disc florets develop acropetally on a capitulum.

Bud:

- *Bud shape*.—Conical.
- *Bud length*.—Approximately 3.5 cm.
- *Bud diameter*.—Approximately 1 cm.
- *Bud color*.—Near RHS Yellow-Green 144 A.

Inflorescence/flower:

- *Diameter of entire flower*.—Approximately 12 cm.
- *Depth of flower*.—Approximately 1.5 cm.
- *Width of disc*.—Approximately 2 cm.
- *Depth of disc*.—Approximately 1.5 cm.
- *Quantity per plant*.—Approximately 15 flowers and buds on a 12 week old plant.

Ray florets:

- *Number of ray florets*.—Avg. 20.
- *Length*.—Approximately 5 cm.
- *Width*.—Approximately 1.5 cm.
- *Apex*.—Acute.
- *Base*.—Attenuate.
- *Shape*.—Oblanceolate.
- *Margin*.—Entire.
- *Texture*.—Glabrous.
- *Aspect*.—Slightly curved.

Color:

- *Ray florets*.—Upper surface at first opening: Near RHS Yellow 12 B, center streaks near Orange-Red N34 A. Upper surface at maturity: Near RHS Yellow 12 A center streaks near Orange-Red N34 A and Red 46 B. Upper surface at fading: Near RHS Yellow 13 B center streaks near Red N34 C. Under surface at first opening: Near RHS Yellow 11 B center streaks near Red N34 B. Under surface at maturity: Near RHS Yellow 11 A center streaks near Red N34 C. Under surface at fading: Near RHS Yellow 13 C center streaks near Red N34 D.

Disc florets:

- *Number of disc florets*.—Approximately 175.
- *Length*.—1 to 1.5 cm.
- *Width*.—0.2 to 0.3 cm.
- *Shape*.—Tubular.
- *Margin*.—Wavy.

Color:

- *At first opening*.—Near RHS Yellow 12 A.
- *At maturity*.—Near RHS Yellow 12 B.
- *At fading*.—Near RHS Yellow 12 C.

Fragrance: No.

Peduncle:

- *Peduncle length*.—Approximately 15 cm.
- *Peduncle diameter*.—Approximately 1 cm.
- *Angle*.—Approximately 90 deg from center of whorl. (Upright).
- *Color*.—Near RHS Green 138 C.
- *Peduncle texture*.—Glabrous.

REPRODUCTIVE ORGANS

Disc florets:

*Androecium*.—Stamens: About 5. Anther shape: Linear. Anther length: Approximately 0.5 cm.

*Gynoecium*.—Pistil number: 1. Pistil shape: Needle. Pistil length: Approx. 0.5 cm. Style length: Approx. 0.5 cm.

Ray florets (if any reproductive structures present):

*Androecium*.—Not present.

*Gynoecium*.—Pistil number: 1. Pistil shape: Needle.

OTHER CHARACTERISTICS

Fruit/seed production: Moderate production of achene type seeds.

*Shape*.—Ovate.

*Color*.—Near RHS Grey-Brown 199B.

*Size*.—2 mm.

What is claimed is:

1. A new and distinct cultivar of *Gazania* plant named 'LOMGAZYLRS' as herein illustrated and described.

* * * * *